United States Patent
Soffiati et al.

(10) Patent No.: US 7,601,176 B2
(45) Date of Patent: Oct. 13, 2009

(54) DISPOSABLE ARTICULATED SPACING DEVICE FOR SURGICAL TREATMENT OF JOINTS OF THE HUMAN BODY

(75) Inventors: Renzo Soffiati, Nogara (IT); Claudio Castelli, Bergamo (IT); Giovanni Faccioli, Monzambano (IT)

(73) Assignee: Tecres S.p.A., Sommacampagna (IT)

( * ) Notice: Subject to any disclaimer, the term of this patent is extended or adjusted under 35 U.S.C. 154(b) by 556 days.

(21) Appl. No.: 10/963,123

(22) Filed: Oct. 12, 2004

(65) Prior Publication Data

US 2005/0085918 A1    Apr. 21, 2005

Related U.S. Application Data

(63) Continuation of application No. 10/239,813, filed as application No. PCT/IB01/00574 on Apr. 9, 2001, now abandoned.

(30) Foreign Application Priority Data

Apr. 7, 2000    (IT)    ................ VI2000U000025

(51) Int. Cl.
*A61F 2/30*    (2006.01)
(52) U.S. Cl. ................................. 623/18.11
(58) Field of Classification Search ............. 623/18.11, 623/19.11, 20.11, 20.14, 20.16–17, 20.2, 623/22.13, 23.28–3, 23.36, 23.46, 23.5, 23.52, 623/23.55, 23.57–6
See application file for complete search history.

(56) References Cited

U.S. PATENT DOCUMENTS

| | | | |
|---|---|---|---|
| 4,462,120 A | | 7/1984 | Rambert et al. |
| 5,123,927 A | | 6/1992 | Duncan et al. |
| 5,344,459 A | * | 9/1994 | Swartz ................ 623/14.12 |
| 5,366,508 A | * | 11/1994 | Brekke ................ 623/23.58 |
| 5,522,895 A | * | 6/1996 | Mikos ................ 623/23.58 |
| 5,650,108 A | * | 7/1997 | Nies et al. ................ 264/122 |
| 5,827,289 A | * | 10/1998 | Reiley et al. ................ 606/86 |
| 5,947,893 A | * | 9/1999 | Agrawal et al. ................ 600/36 |
| 5,980,573 A | | 11/1999 | Shaffner |
| 6,007,580 A | * | 12/1999 | Lehto et al. ................ 623/21.11 |
| 6,027,743 A | * | 2/2000 | Khouri et al. ................ 424/423 |
| 6,113,640 A | * | 9/2000 | Tormala et al. ................ 623/18.11 |
| 6,206,927 B1 | * | 3/2001 | Fell et al. ................ 623/20.29 |

(Continued)

FOREIGN PATENT DOCUMENTS

DE    297 03 971.7    7/1998

(Continued)

*Primary Examiner*—Eduardo C Robert
*Assistant Examiner*—David Comstock
(74) *Attorney, Agent, or Firm*—R. Neil Sudol; Henry D. Coleman; William J. Sapone (57) ABSTRACT

A disposable articulated spacing device for use as a temporary joint prosthesis includes a first member secured during an implantation procedure to a first articulation end and a separate and independent second member secured separately during the implantation procedure to the other articulation end, both members being pre-formed and made entirely of biological compatible and porous material suitable to be added with pharmaceutical and therapeutical products. The pre-formed members are reciprocally coupled in an articulated manner to maintain a suitable joint space and at least a partial articulation for the time necessary to perform the further implantation of a joint prosthesis.

18 Claims, 6 Drawing Sheets

U.S. PATENT DOCUMENTS

| | | | |
|---|---|---|---|
| 6,210,436 B1 * | 4/2001 | Weadock | 623/1.39 |
| 6,280,475 B1 * | 8/2001 | Bao et al. | 623/17.16 |
| 6,328,765 B1 * | 12/2001 | Hardwick et al. | 623/23.72 |
| 6,398,814 B1 * | 6/2002 | Paasimaa et al. | 623/23.51 |
| 6,410,044 B1 * | 6/2002 | Chudzik et al. | 424/423 |
| 6,419,704 B1 * | 7/2002 | Ferree | 623/17.12 |
| 6,419,709 B1 * | 7/2002 | Mao et al. | 623/23.58 |
| 6,454,811 B1 * | 9/2002 | Sherwood et al. | 623/23.76 |
| 6,508,838 B2 * | 1/2003 | Lee et al. | 623/11.11 |
| 6,514,286 B1 * | 2/2003 | Leatherbury et al. | 623/11.11 |
| 6,719,989 B1 * | 4/2004 | Matsushima et al. | 424/422 |
| 2001/0018614 A1 * | 8/2001 | Bianchi | 623/16.11 |
| 2002/0013626 A1 * | 1/2002 | Geistlich et al. | 623/23.57 |
| 2003/0033021 A1 | 2/2003 | Plouhar et al. | |
| 2003/0114936 A1 * | 6/2003 | Sherwood et al. | 623/23.58 |
| 2004/0030341 A1 * | 2/2004 | Aeschlimann et al. | 606/72 |
| 2004/0267363 A1 * | 12/2004 | Fell et al. | 623/14.12 |

FOREIGN PATENT DOCUMENTS

| | | |
|---|---|---|
| EP | 0 811 359 A2 | 12/1997 |

\* cited by examiner

# DISPOSABLE ARTICULATED SPACING DEVICE FOR SURGICAL TREATMENT OF JOINTS OF THE HUMAN BODY

TECHNICAL FIELD

The present invention is generally applicable to surgical treatment of articulations of the human body and in particular relates to a disposable spacing device for temporary replacement of joint prosthesis which have to be explanted due to unsuccessful septic or aseptic implantation of artificial joints.

According to the well known surgical "dual stage" method, the above spacing device can be maintained in the joint seat as long as necessary for re-establishing the most favourable conditions of implantation of the new artificial joint prosthesis.

BACKGROUND ART

It is known how artificial joints, such as knee, hip, heel and elbow joints often have to be removed for various reasons and mainly following local infections after a surgical implant.

In such a case, it is not possible to replace immediately the unsuccessful prosthesis with a new one, but the seat of the joint must be treated with suitable antibiotics before a new surgical operation can be performed.

In the meantime, the space within the joint must be maintained in order to prevent a reduction in the articular space, retraction of the tissues, atrophying of the joint and loss of muscular elasticity and tone.

Spacing devices used in the two-stage implant of artificial joints, for treatment of both the hip and the knee, are known.

Italian patent application No. VR95A000072 describes a disposable spacing device for an artificial hip joint, essentially characterized in that it is made of a biocompatible base material of the type used for bone cements.

Spacing devices for knee joints which are manually made by the surgeon at the time of the surgical operation are also known, these devices being made from blocks of bone cement of standard shape, optionally containing active constituents.

A drawback of these known methods of treatment is that they do not allow the space within the joint to be kept apart in an ergonomically and anatomically correct manner. Moreover, the long time required for preparation increases the difficulties for the surgeon and reduces the probability of success of the operation.

In order to overcome these drawbacks, spacing devices have been made using suitable anatomically and ergonomically shaped moulds which are filled with bone cement in situ. However, these known spacing devices do not allow mobilisation of the joint and result in the need for a long rehabilitation after reimplanting the permanent prosthesis.

In still other cases, the spacing devices have been obtained by lining a permanent metal prosthesis with bone cement. Although this solution allows a temporary articulation, it is difficult to prepare and in spite of use of cement-lined prostheses requires that such devices are positioned in infected seats, which most of the surgeon consider a worsening infection factor.

DISCLOSURE OF THE INVENTION

The main object of the present invention is to provide surgeons with a disposable and ready-to-use articulated spacing device, able to be directly implanted in the articulation seat for example of knee, hip, hell or elbow joints in case of replacement of a pre-existing prosthesis which must be removed due to septic or aseptic failures.

A further object is to provide a disposable articulated spacing device which allows to maintain a in a healing environment a suitable articular space for the time necessary to successfully re-implant a new permanent prosthesis.

A further object is to provide a disposable articulated spacing device which allows correct articulation and an anatomical and ergonomic form of the temporary implant.

Yet another object is to provide a disposable articulated spacing device which can be easily implanted and explanted into/from the location of the joint.

Yet another object is to provide a disposable articulated spacing device with limited articular friction so as to allow considerable mobility of the joint and improve the quality of life of the patient during hospitalisation.

These and other objects which will be more apparent hereinafter are achieved by a disposable articulated spacing device for the temporary replacement of a joint of the human body which, in accordance with claim 1, comprises at least one first member able to be secured to a first articulation end and at least one second member able to be secured to a second articulation end, both said members being pre-formed and entirely made of biological compatible and porous material suitable to be added with pharmaceutical and therapeutical products, said pre-formed members being able to be reciprocally coupled in an articulated manner to maintain a suitable joint space and at least partial articulated mobility for the time necessary to perform the further implantation of a new permanent joint prosthesis.

Preferably, the above mentioned biologically compatible and porous material is chosen from among metals, metallic alloys, organo-metals, ceramics, glasses, plastics materials, bone cements and combinations thereof. These materials are rigid materials, the insert members being implanted in their preformed or manufactured shapes, without conformational alteration at the time of implantation.

The pre-formed members of the device may be previously charged with suitable pharmaceutical and therapeutical products. As alternative, the pre-formed members are initially free of the same products and are added immediately prior of their implantation by contact absorption or by filling of suitable cavities formed on their other surface.

Advantageously, the pharmaceutical and therapeutical products may be chosen among medical active principles, antibiotics and radiopacifier and may be added in the pre-formed members In case that the articulated spacing device replaces a knee joint, the pre-formed members may comprise a femoral member consisting of a body substantially shell-shaped and reproducing the femoral condyles, and tibial members consisting of a prismatic body able to replace the resected tibial flat portion.

BRIEF DESCRIPTION OF THE DRAWINGS

Further features and advantages of the invention will, be more clearly understood in the light of the following detailed description of a disposable articulated spacing device furnished by way of a non-limiting example with the aid of the accompanying drawings, in which.

DETAILED DESCRIPTION OF PREFERRED EMBODIMENTS

Figure 1:
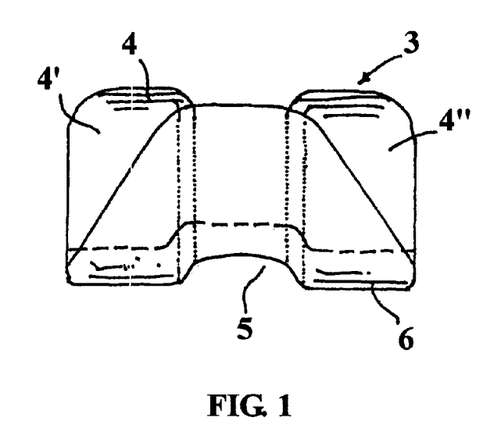
FIG. 1 shows a front view of a first detail of a spacing model according to the invention.
Figure 2:
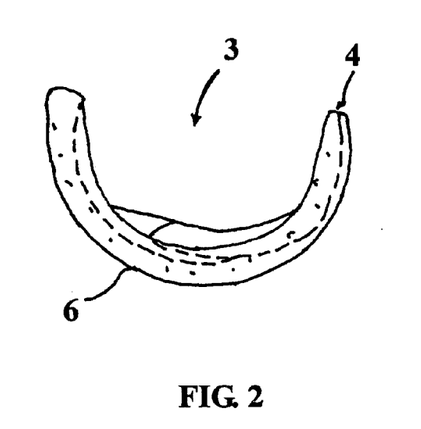
FIG. 2 shows a side view of the detail according to FIG. 1.
Figure 3:
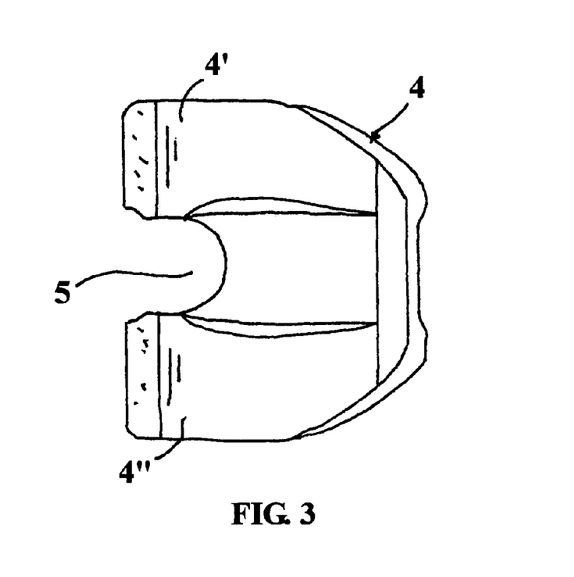
FIG. 3 shows a top view of the detail according to FIG. 1.
Figure 4:
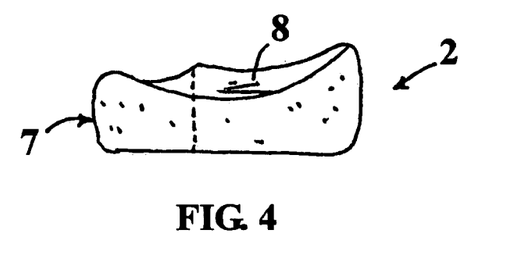
FIG. 4 shows a front view of another detail of the spacing device according to the invention.
Figure 5:
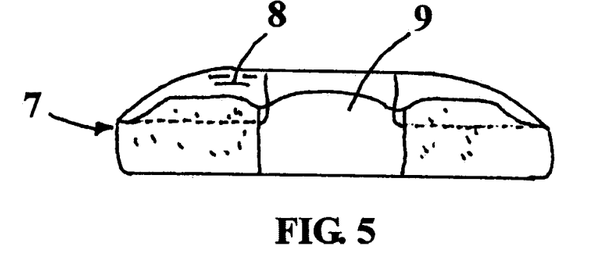
FIG. 5 shows a side view of the detail according to FIG. 4.
Figure 6:
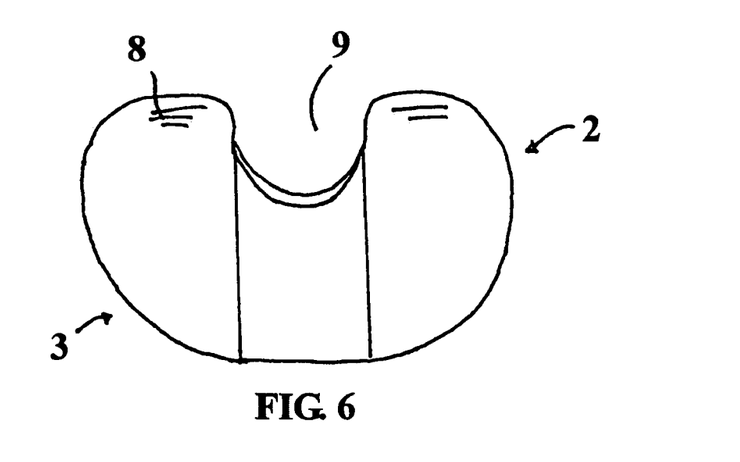
FIG. 6 shows a top view of the detail according to FIG. 4.
Figure 7:
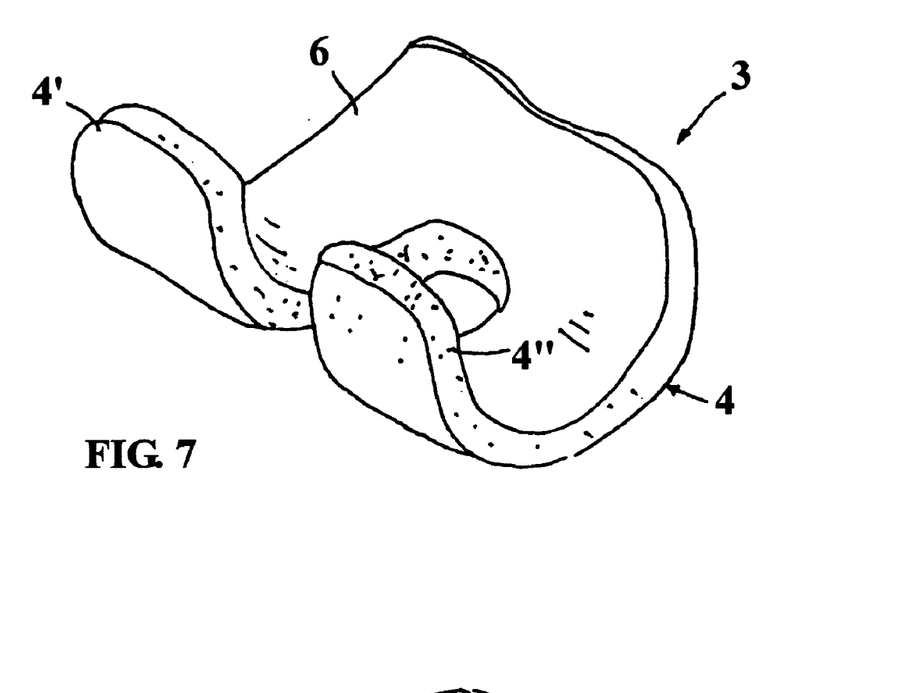
FIGS. 7 and 8 show perspective views, from the top and bottom, of the detail of the device illustrated in FIGS. 1 to 3.
Figure 8:
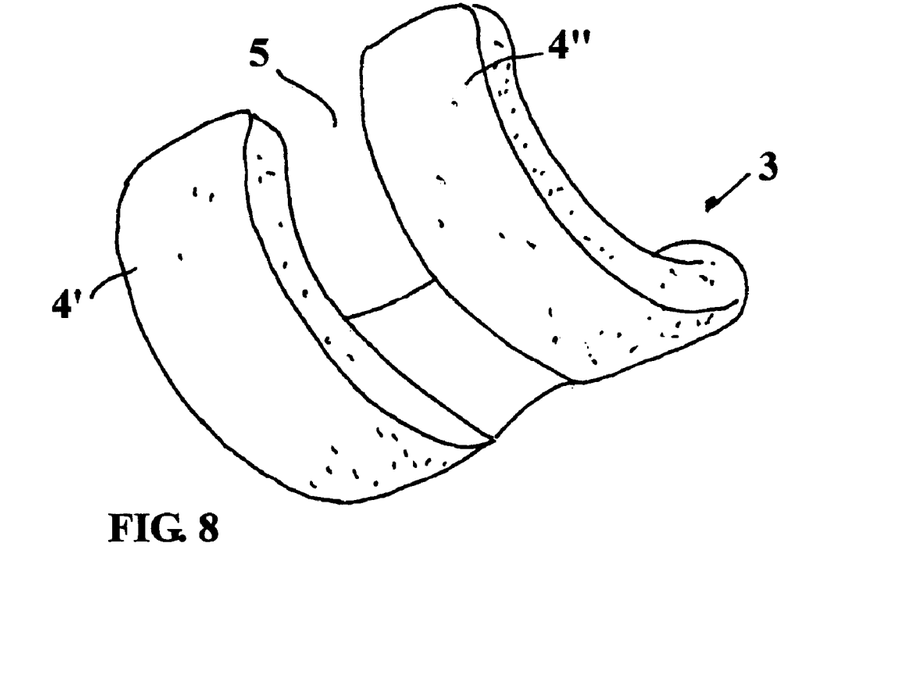
Figure 9:
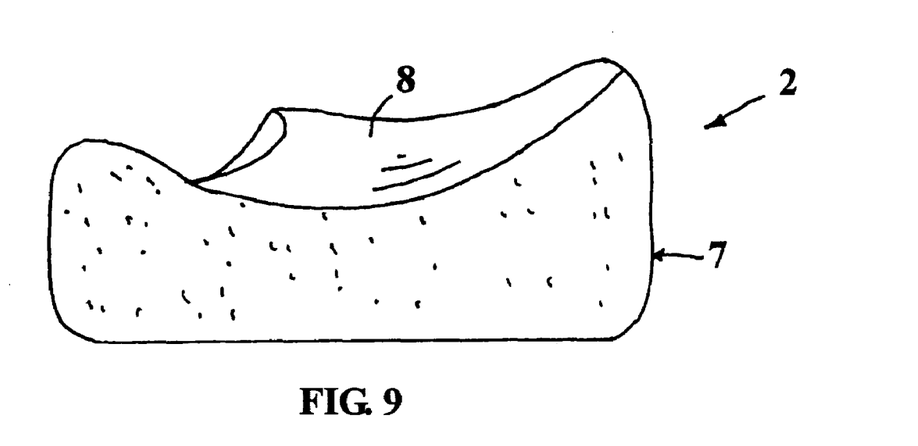
FIGS. 9 and 10 show a side view and a top perspective view of the detail according to FIGS. 4 to 6.
Figure 10:
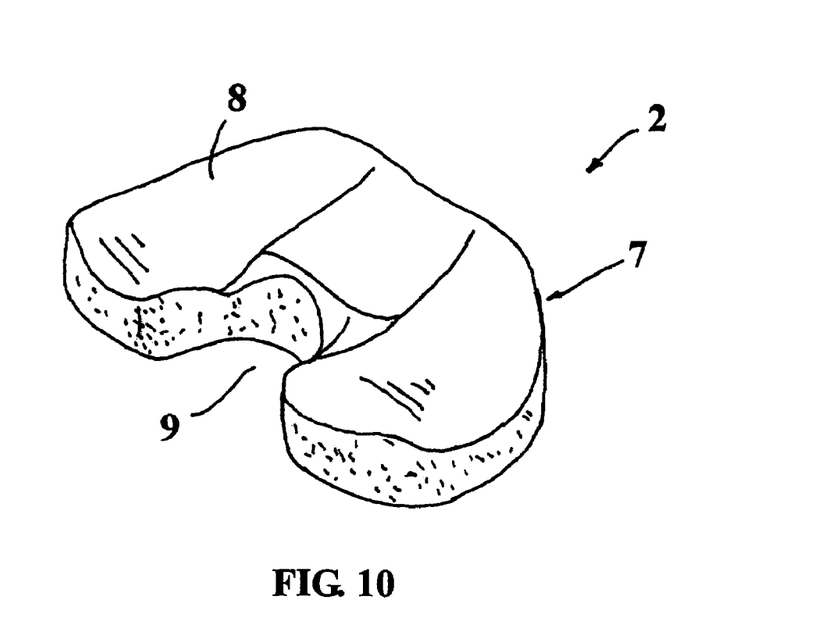
Figure 11:
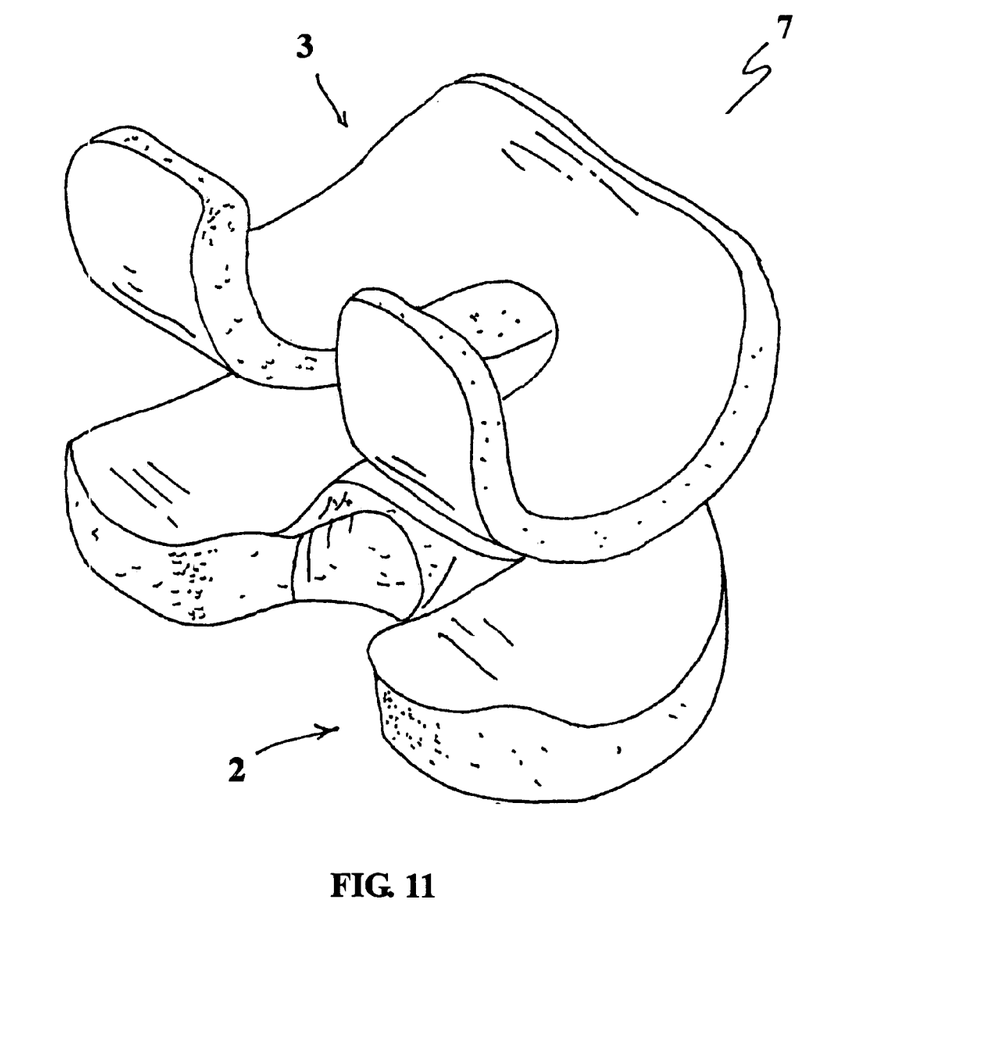
FIG. 11 shows a perspective view of the two details of the preceding figures in aligned positions.
Figure 12:
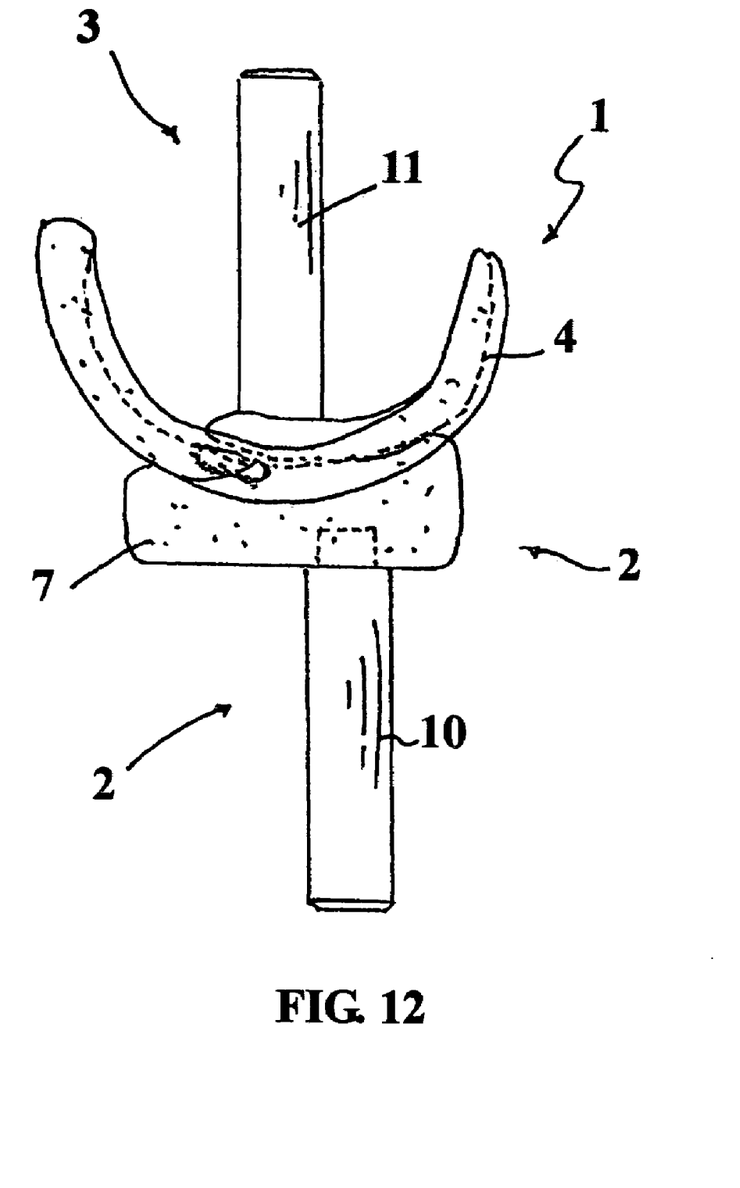
FIG. 12 shows a side view of an alternative embodiment of the spacing device according to the invention.

With reference to the above mentioned figures, there is shown a disposable articulated spacing device for the temporary replacement of a joint prosthesis explanted from a human body.

The articulated spacing device, generally indicated with the reference number 1, comprises at least one first member 2 able to be secured to a first joint end and at last one second member 3 able to be secured to a second joint end.

According to the invention, both members 2, 3 are preformed and entirely made of a biological compatible and porous material and are mutually coupled in an articulated manner so as to maintain in a healing environment a suitable joint space and at least partial mobility of the joint for the time necessary to permit the further re-implantation of a new permanent joint prosthesis.

Preferably, the biological compatible and porous material may be chosen among metals, metallic alloys organo-metals, ceramics, glasses, plastics materials and combinations thereof.

Specifically, the above plastics material may be chosen among thermoplastic polymers, such as acrylic resins, polyethylene, polypropylene, thermoformable e.g. by blow moulding or injection moulding.

As alternative, the plastics material may be chosen among cold-formable resins curable by means of free radical polymerisation such as acrylic resins and polyesters.

In a per se known manner, free radical polymerisation may be accelerated either by suitable chemical catalysts and initiators, such as benzoyl peroxide, or physical accelerators such as ionizing radiation, gamma-rays, UV-rays.

In the particularly preferred embodiment the biological compatible and porous material forming the members 2, 3 is a bone-cements, e.g. that used in the Italian patent application no. VR95A000072 filed by the same applicant.

The pre-formed members 2, 3 may be previously added with suitable pharmaceutical and therapeutical products chosen among active medical principles, antibiotics and radio-pacifiers.

In alternative, the pharmaceutical and therapeutical products may be added to the pre-formed members immediately prior of implantation thereof either by direct contact absorption or by filling of suitable cavities formed on their outer surfaces.

The pharmaceutical and therapeutical products in the form of liquid solutions may be easily absorbed by the device thanks to the porosity of their basic material and then released after implantation in the joint seat.

Advantageously, the pre-formed members 2, 3 may be shaped in different standard sizes to be correctly adapted to the different patients. Moreover, these members may present anchoring means for their fixation to the joint ends The embodiment of the spacer device 1 shown in the figures is designed to be inserted in the knee joint.

The pre-formed member 2 is a tibial member and the pre-formed member 3 is a femoral member.

In particular, the femoral part 3 consists of a first proximal body 4 designed to occupy the space left by an explanted metal prosthesis. Preferably, the body 4 has a shape, in plan view, approximately in the form of a "U" or horseshoe, with side portions 4', 4" and a central recess 5. The external contact surface 6 of the body 4 has a curvature able to reproduce that of the femoral condyles.

The tibial member 2 consists of a second proximal body 7 which is approximately prismatic, slightly curved and of suitable thickness. The body 7 also has a shape, in plan view, approximately in the form of a "U" or horseshoe, with a curved internal contact surface 8 and an internal recess 9 so as to simulate the resected tibial flat portion.

The contact surfaces 6, 8 of members 2, 3 are formed so as to allow a roto-translatory movement during the flexing/extending movement of the limb.

Moreover, the surfaces 6, 8 may have an excellent surface finish with a low coefficient of friction so as to allow a considerably degree of articular mobility.

Both members 2, 3 may be provided with respective projections or rod-shaped distal portions 10, 11 for securing to the respective joint ends, e.g. by means of bone cement.

In use, the surgeon initially removes the previous infected joint prosthesis and cleans the articulation space. The surgeon further chooses the suitable spacing device with pre-formed members 2, 3 adapted of the size of the patient.

If the pre-formed members are already previously charged with active principles and pharmaceutical and therapeutical products upon formation thereof, the surgeon implants them taking care that they are fixedly secured to the joint ends and are mutually articulately coupled to allow at least partial mobilisation of the joint. Pre-formed members 2, 3 are distinct objects, separate from and independent of one another prior to implantation into the patient and coupling to respective articulation ends. Accordingly, members 2, 3 are inserted separately into the patient in seriatim.

If on the contrary the members are not yet charged as above, the surgeon either impinges them in a solution of active principles or fills with them several outer cavities formed in situ or pre-shaped on their outer surfaces, and finally implants the members in the articulation seat, securing them to the joint ends through appropriate anchoring means or bone cement.

The invention claimed is:

1. A method for treating joints of the human body, particularly for temporary replacing an explanted permanent joint prosthesis, comprising:

providing a preformed disposable articulated spacing device including at least one pre-formed first member and at least one pre-formed second member both made entirely of biologically compatible and porous material, said first member and said second member being distinct bodies independent of and separate from one another, said first member and said second member having a porosity in their base material or suitable cavities formed on their outer surfaces adapted to be filled with pharmaceutical and therapeutical products in the form of liquid solutions, said first member and said second member being initially free of pharmaceutical and therapeutical products;

adding pharmaceutical and therapeutical products in the form of liquid solutions to said first member and said second member either by direct contact and absorption or by insertion thereof in said suitable cavities;

after the adding of said liquid solutions to said first member, inserting said first member into a patient and securing said first member to a first articulation end in the patient;

after the adding of said liquid solutions to said second member, inserting said second member into the patient and securing said second member to a second articulation end in the patient, said second member being inserted into the patient separately from said first member and after the inserting of said first member; and reciprocally coupling said first member and said second member to one another in an articulated manner to maintain a suitable joint space and at least partial articulated mobility for the time necessary to perform the further implantation of a new permanent joint prosthesis.

2. Method according to claim 1, wherein said biologically compatible and porous material is selected from the group consisting of metals, metallic alloys, organo-metals, ceramics, glasses, plastics materials, bone cements and combinations thereof.

3. Method according to claim 2, wherein said plastics materials are selected from the group consisting of thermoplastic polymers, acrylic resins, polyethylene, polypropylene, and resins thermoformable by blow molding or injection molding.

4. Method according to claim 2, wherein said plastics materials are cold-formable resins.

5. Method according to claim 1, wherein said biologically compatible and porous material is a bone cement.

6. Method according to claim 1, wherein said pharmaceutical and therapeutical products are selected from the group consisting of active medical principals, antibiotics and radiopacifiers.

7. Method according to claim 1, wherein said first member and said second member are configured so as to allow a roto-translatory movement of condyles during a flexing/extending movement of a limb.

8. Method according to claim 7, wherein said first member and said second member have respective contact surfaces with a minimum coefficient of friction so as to allow a high degree of articular mobility.

9. Method according to claim 1, wherein said first member and said second member each have one of a plurality of predetermined different sizes adapted to fit patients or different size requirements.

10. Method according to claim 1, further comprising anchoring said first member and said second member to the articulation ends via anchoring means provided on said first member and said second member.

11. Method according to claim 10, wherein said anchoring means consist of respective projections or rod shaped distal portions.

12. Method according to claim 1, further comprising joining said first member and said second member to said joint ends with bone cement.

13. Method according to claim 1, wherein said first articulation and said second articulation are in a knee joint, said first member and said second member comprising a femoral member and a tibial member.

14. Method according to claim 13, wherein said femoral member consists of a first body substantially in the shape of a shell to reproduce femoral condyles and that said tibial member consists of a second body of substantially prismatic shape with predetermined thickness to replace a resected tibial flat portion.

15. Method according to claim 1, wherein said first member and said second member are rigid members.

16. Method according to claim 15, wherein said first member and said second member are of standard sizes.

17. Method according to claim 1, wherein the securing of said first member and said second member to said first articulation end and said second articulation end includes securing said first member and said second member in their respective preformed shapes to said first articulation end and said second articulation end.

18. A disposable articulated method for temporarily replacing an explanted permanent joint prosthesis, comprising:

providing at least one preformed first member ane at least one preformed second member, said first member and said second member being independent of and separate from one another;

inserting said at least one preformed first member into a patient and securing said at least one preformed first member to a first articulation end in the patient; and inserting said at least one preformed second member into the patient and securing said at least one preformed second member to a second articulation end in the patient, said at least one preformed second member being inserted into the patient separately from said at least one preformed first member and after the inserting of said at least one preformed first member, both said first member and said second member being made entirely of biological compatible and porous material suitable for receiving a pharmaceutical or therapeutic agent, reciprocally coupling said first member and said second member in an articulated manner to maintain a suitable joint spacing and at least partial articulated mobility for a time necessary to perform implantation of a new permanent joint prosthesis, said first member and said second member being initially free of pharmaceutical and therapeutic products, immediately prior to implantation of said first member and said second member in a patient, adding, to said first member and said second member, pharmaceutical and therapeutic agents in the form of liquid solutions, either by direct contact and absorption or by insertion thereof in suitable cavities of said first member and said second member.

* * * * *

UNITED STATES PATENT AND TRADEMARK OFFICE
CERTIFICATE OF CORRECTION

PATENT NO. : 7,601,176 B2  Page 1 of 1
APPLICATION NO. : 10/963123
DATED : October 13, 2009
INVENTOR(S) : Soffiati et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Fifth Day of October, 2010

David J. Kappos
*Director of the United States Patent and Trademark Office*